United States Patent
Lee et al.

(10) Patent No.: US 9,533,896 B2
(45) Date of Patent: Jan. 3, 2017

(54) FLUID STERILIZER AND ASSOCIATED CONNECTING DEVICE

(71) Applicant: Seoul Viosys Co., Ltd., Ansan-si (KR)

(72) Inventors: Seong Min Lee, Ansan-si (KR); Young Hwan Son, Ansan-si (KR); Jae Seon Yi, Ansan-si (KR); Jong Rack Kim, Ansan-si (KR); Ik Hwan Ko, Ansan-si (KR)

(73) Assignee: SEOUL VIOSYS CO., LTD., Ansan-Si (KR)

( * ) Notice: Subject to any disclaimer, the term of this patent is extended or adjusted under 35 U.S.C. 154(b) by 0 days.

(21) Appl. No.: 14/479,186

(22) Filed: Sep. 5, 2014

(65) Prior Publication Data

US 2015/0060693 A1    Mar. 5, 2015

(30) Foreign Application Priority Data

Sep. 5, 2013  (KR) .......................... 10-2013-0106872
Aug. 20, 2014  (KR) .......................... 10-2014-0108121

(51) Int. Cl.
*C02F 1/32*    (2006.01)

(52) U.S. Cl.
CPC ......... *C02F 1/325* (2013.01); *C02F 2201/003* (2013.01); *C02F 2201/3222* (2013.01); *C02F 2201/3227* (2013.01); *C02F 2201/3228* (2013.01); *C02F 2303/04* (2013.01)

(58) Field of Classification Search
CPC ....................... C02F 1/32; C02F 1/325; C02F 2201/32–2201/328; C02F 2201/003; C02F 2303/04; A61L 2/10; A61L 2/08
USPC ................ 250/428, 432 R, 435; 422/22, 24; 210/748.1, 748.11
See application file for complete search history.

(56) References Cited

U.S. PATENT DOCUMENTS

| 4,267,455 A | * | 5/1981 | Keller ....................... A61L 2/10 210/192 |
| 2004/0222163 A1 | * | 11/2004 | Saccomanno ............. A61L 2/10 210/748.11 |
| 2007/0125960 A1 | * | 6/2007 | Chen ......................... A61L 2/10 250/455.11 |
| 2008/0280227 A1 | * | 11/2008 | Sievers ................. G03F 7/2057 430/270.1 |
| 2010/0078574 A1 | * | 4/2010 | Cooper .................. B01J 19/123 250/455.11 |
| 2010/0237254 A1 | * | 9/2010 | Mason ...................... A61L 2/10 250/435 |
| 2011/0084011 A1 | * | 4/2011 | Miller ..................... C02F 1/325 210/198.1 |
| 2011/0226966 A1 | * | 9/2011 | Takahashi .............. A01K 63/04 250/492.1 |
| 2014/0105784 A1 | * | 4/2014 | Smeeton ................ B01J 19/123 422/24 |

FOREIGN PATENT DOCUMENTS

KR    1020120134809 A    7/2013

* cited by examiner

*Primary Examiner* — David E Smith
(74) *Attorney, Agent, or Firm* — Perkins Coie LLP

(57) ABSTRACT

A sterilizer may include: a first pipe having an inner wall with a light reflecting property; a second pipe disposed in the first pipe so as to pass fluid therethrough and formed of a light transmitting material; and a plurality of UV LEDs arranged on the inner wall of the first pipe and configured to irradiate sterilization UV light onto the fluid.

10 Claims, 11 Drawing Sheets

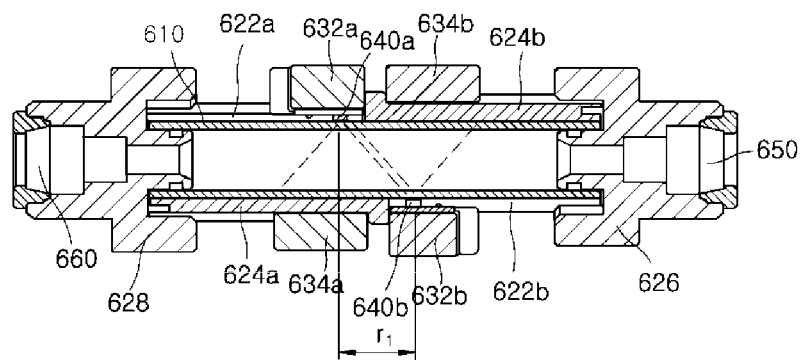
FIG 7A
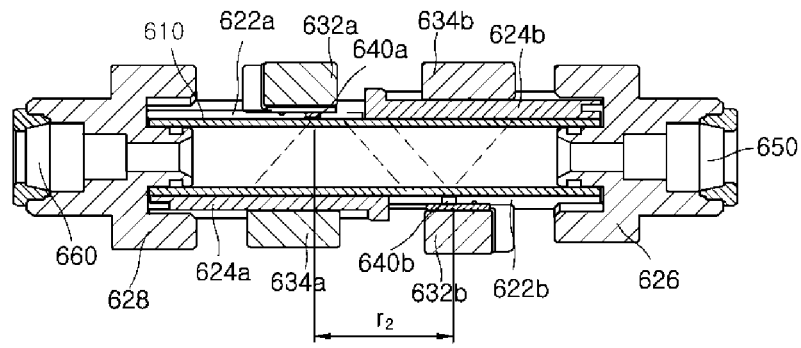
FIG 7B
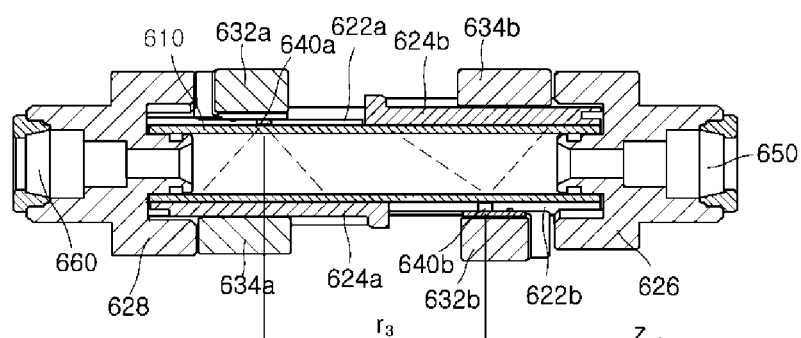
FIG 7C
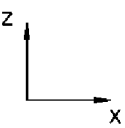

FLUID STERILIZER AND ASSOCIATED CONNECTING DEVICE

CROSS-REFERENCES TO RELATED APPLICATIONS

This patent document claims priorities to, and benefits of, prior Korean application numbers 10-2013-0106872 and 10-2014-0108121 that are filed on Sep. 5, 2013 and Aug. 20, 2014, respectively, and incorporates the above Korean filings by reference in their entirety.

BACKGROUND

The technology disclosed in this patent document relates to a sterilizer, including a fluid sterilizer and an associated connecting device.

Due to the recent concern about water pollution caused by environmental contamination, the demand for a water purifier has increased. There are various kinds of water purifiers available, such as a natural filtration water purifier, a direct-connection filtration water purifier, an ion-exchange resin water purifier, a distillation water purifier, a reverse osmosis water purifier and others, according to the water purification techniques or processes used for water purification.

Recently, there have emerged water purifiers which directly sterilize water using ultra-violet (UV) light. Many conventional water purifiers using UV light use an underwater UV light source. Such a conventional water purifier, in one example, fills a container with water to be sterilized, and turn on a UV light source dipped or submerged in the water to sterilize the water. The conventional water purifier has advantages in that the installation can be completed by dipping or submerging the UV light source in the container filled with the water, the equipment can be reduced in size, and the installation cost can be saved. However, the conventional water purifier may require a considerable reaction time for irradiating UV light to sterilize water, or may not uniformly sterilize all the water in the container.

One example of such a conventional water purifier using UV light is disclosed in Korean Patent Publication No. 2012-0134809 and entitled "Water purifier".

SUMMARY

Embodiments of the disclosed technology are directed to a sterilizer capable of shortening a reaction time and improving sterilization uniformity in sterilizing a fluid such as water and a connector using the same.

In one embodiment, a sterilizer for sterilizing a fluid may include: a first pipe having an inner wall that reflects ultraviolet (UV) light; a second pipe disposed in the first pipe to pass a fluid therethrough and formed of a light transmitting material to allow the UV light to enter the second pipe to illuminate and to sterilize the fluid; and a multiple number of UV light emitting diodes (LEDs) arranged on the inner wall of the first pipe and configured to irradiate sterilization UV light onto the fluid.

In another embodiment, a sterilizer for sterilizing a liquid may include: a first pipe having a closed end and an opposite, open end; a second pipe disposed in the first pipe and having a light transmitting property to transmit ultraviolet (UV) light; and a multiple number of UV light sources engaged to and arranged in the first pipe and configured to provide UV light to a fluid flowing through the inside of the second pipe or the space between the first and second pipes to cause sterilization of the fluid.

In another embodiment, a connector having a function of sterilizing a liquid may include: a first pipe having an inner wall that reflects ultraviolet (UV) light; a multiple number of UV LEDs arranged on the inner wall that produce UV light; a second pipe disposed in the first pipe to pass a fluid therethrough, and structured to transmit the UV light from the UV LEDs into an interior of the second pipe to cause sterilization of the fluid; and connection parts on both ends of the connector to connect two external fluid flow pipes to guide the fluid between the two external fluid flow pipes.

In another embodiment, a sterilizer for sterilizing a fluid may include: a light-transmitting fluid flow pipe having a side wall that transmits ultraviolet (UV) light to a fluid inside the light-transmitting fluid flow pipe to be sterilized; movable units mounted outside of the light-transmitting fluid flow pipe; and UV light sources mounted on the movable units to provide UV light for sterilizing the fluid flowing through the light-transmitting fluid flow pipe. The movable units may adjust the distance between the UV light sources on the body part.

In various implementations of the present disclosure, while a fluid flows through the first or second pipe, the fluid may be sterilized by the UV LEDs. Since the UV LEDs may be reduced in size, they can be easily installed on the inner wall of the first pipe.

Furthermore, by sterilizing a fluid passing through the pipe, the covering area of the UV light may be increased. In addition, the UV light can be provided to the entire fluid by installing a light reflecting structure. Thus, non-irradiation area to which the UV light is not reached does not exist in the fluid.

BRIEF DESCRIPTION OF THE DRAWINGS

FIGS. 7A to 7C illustrate an example of an arrangement of the UV light sources of the sterilizer in accordance with the disclosed technology.

DESCRIPTION OF SPECIFIC EMBODIMENTS

Figure 1A:
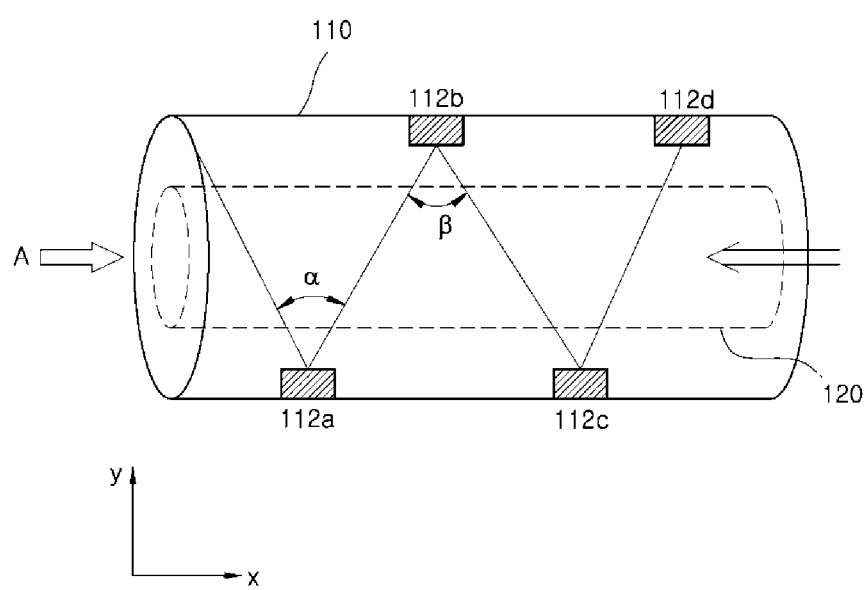
FIG. 1A schematically illustrates an example of a sterilizer in accordance with a first embodiment of the disclosed technology.

Embodiments of the disclosed technology will hereinafter be described in detail with reference to implementation examples, including those illustrated in the accompanying drawings. It should be noted that the drawings are not to precise scale and may be exaggerated in thickness of lines or sizes of components for descriptive convenience and clarity only.

In describing various embodiments of the present disclosure, when an element is referred to as being positioned on another element or over, under, and at a side of another element, it may indicate the relative positional relationship therebetween. Thus, the former element may be directly contacted with the latter element, or an additional element may be interposed at the interface therebetween. Furthermore, when an element is referred to as being coupled or connected to another element, it may indicate that the former element is directly coupled or connected to the latter element or an additional element is interposed therebetween. Throughout the specification, like reference numerals denote substantially the same components.

In the present specification, the term "pipe" indicates a kind of tube or a pipe-shaped structure, and may include a structure capable of passing fluid through an internal space thereof. The "pipe" may have a cross-section formed in a circular shape or polygonal shape.

Furthermore, "beam angle" may indicate an emission angle at which a light intensity corresponding to 50% or more of the maximum light intensity is obtained, in light emitted from an LED (light emitting diode) chip forming an LED.

A sterilizer in accordance with an embodiment of the disclosed technology includes a first, outer pipe and a second, inner pipe inside the first pipe, forming a dual pipe structure where the inner wall of the first pipe is used to support UV light sources and the second pipe is used to transport the fluid to be sterilized. The sterilizer may have a pipe shape to pass a fluid or a fitting that is shaped to connect a pipe to another pipe.

Figure 1B:
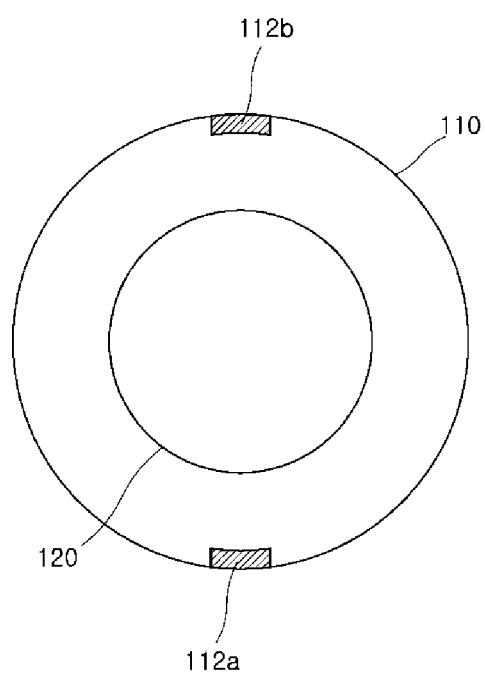
FIG. 1B is a plan view of the sterilizer of FIG. 1A, seen from a direction A.

FIG. 1A schematically illustrates an example of a sterilizer in accordance with a first embodiment of the disclosed technology. FIG. 1B is a plan view of the sterilizer of FIG. 1A, seen from a direction A. Referring to FIGS. 1A and 1B, the sterilizer 100 includes a first pipe 110 as the outer pipe and a second pipe 120 as the inner pipe located inside the first pipe. The inner hollow space inside the second pipe 120 is used to carry and transport a fluid (such as water) to be sterilized under illumination of UV light. The first pipe 110 may include an inner wall having a light reflecting property, thus reflecting light. For example, in one implementation, the inner wall of the first pipe 110 may be coated with a metal having a high reflectance, such as aluminum or silver. In another implementation, the first pipe 110 may be formed of, or may include, a metal having a high reflectance, such as aluminum or silver.

The first pipe 110 may include, or be structured to engage to, UV light sources 112a, 112b, 112c, and 112d which may be arranged on the inner wall of the first pipe 110. The UV light sources 112a, 112b, 112c, and 112d emit UV light with a wavelength suitable for sterilization, e.g., in a UV spectral range of about 200 nm to 400 nm. More specifically, in some implementations, the UV light sources 112a, 112b, 112c, and 112d may emit UV light with a wavelength of about 200 nm to 290 nm for sterilization. The UV light sources 112a, 112b, 112c, and 112d are arranged to collectively produce the UV light that fills the interior of the second pipe 120 carrying and transporting the fluid to be sterilized and to provide effective illumination for sterilization.

In an embodiment, the UV light sources 112a, 112b, 112c, and 112d may include UV LEDs. The UV LEDs 112a, 112b, 112c, and 112d may be arranged in a zigzag pattern on the inner wall of the first pipe 110 in consideration of the beam angles of UV beams emitted by the UV LEDs in order to provide desired UV illumination coverage within the fluid-carrying second pipe 120 for effective sterilization of the fluid. As shown in FIG. 1B, some of the UV LEDs may be arranged on opposite sides of the second pipe 120 and, as shown in FIG. 1A, the UV LEDs may be spaced from one another along the elongated direction (i.e., X-axis direction as labeled) while still providing sufficient UV illumination inside the second pipe 120 for effective sterilization. Referring to FIG. 1A, for example, the UV LED 112b located on one side of the second pipe 120 may be positioned within the beam angle α of the light emission or the output UV beam of the UV LED 112a located on the opposite side of the second pipe 120, and, similarly, the UV LED 112c on the same side of the second pipe 120 with the UV LED 112a may be positioned within the beam angle 13 of the light emission of the output UV beam of the UV LED 112b which is, along with the UV LED 112d, on the opposite side of the second pipe 120. This arrangement of the UV LEDs would ensure the UV light beams emitted by the UVLEDs to have some spatial overlap to fill up the interior space inside the second pipe 120 without leaving any space that is not illuminated by the UV light so that the fluid inside the second pipe 120 is fully illuminated by the UV light for the sterilization operation. In some implementations, for example, the beam angle α or β may range from about 110° to 140°. FIGS. 1A and 1B illustrate four UV LEDs 112a, 112b, 112c, and 112d, but in other implementations, the number of UV LEDs arranged along the X-axis direction corresponding to the longitudinal direction of the first pipe 110 is not limited to the illustrated example and can vary depending on the longitudinal length along the second pipe 120 for desired sterilization.

Referring to FIGS. 1A and 1B, the UV LEDs 112b and 112d may be arranged on the top inner wall of the first pipe 110 along the X-axis direction or the longitudinal direction of the first pipe 110, and the UV LEDs 112b and 112d may be arranged on the bottom inner wall of the first pipe 110 along the X-axis direction. However, other implementations are also possible. As long as the UV LEDs 112a, 112b, 112c, and 112d are arranged along the X-axis direction to satisfy the above-described condition in which one UV LED is positioned within the beam angle of another UV LED, the UV LEDs 112a, 112b, 112c, and 112d may be arranged in various manners on the inner wall of the first pipe 110.

In the example in FIGS. 1A and 1B, the second pipe 120 is disposed inside the first pipe 110 so as to pass the fluid to be sterilized through the UV illumination section to achieve sterilization. The second pipe 120 may be formed of a light transmitting material which allows the UV light to transmit through the walls of the second pipe 120 to reach the fluid inside the second pipe 120 for the sterilization operation. For example, the second pipe 120 may be formed of, or include, a quartz pipe. Thus, UV light generated from the UV light sources 112a, 112b, 112c, and 112d arranged on the inner wall of the first pipe 110 may penetrate the second pipe 120, and supply the UV light to the fluid. The UV light irradiated into the second pipe 120 can sterilize the fluid.

Although not illustrated, the sterilizer 100 may include a driving device provided at one end or both ends thereof so as to generate a driving force that causes the fluid to follow through the second pipe 120. The driving device may include, for example, a fluid treatment pump. The driving device may control the flow velocity and rate of the fluid.

As described above, the sterilizer sterilizes the fluid using the UV light sources by making the fluid flow through the UV illuminated section of the second pipe 120. Since the UV LEDs are used as the UV light sources, the UV light sources may be reduced in size and easily installed on the inner wall of the first pipe 110. In addition, UV LEDs provide energy efficient UV light production than other UV light sources.

In accordance with the embodiments of the disclosed technology, since the sterilizer sterilizes a fluid by making the fluid pass through the pipe, the sterilizer may be configured to uniformly irradiate UV light on the fluid. Thus, the sterilizer may prevent the occurrence of a non-irradiation area within the fluid, onto which the UV light is not irradiated, while a non-irradiation area occurs in the conventional underwater sterilizers. Furthermore, since the sterilization is performed in a state where fluid is passed through the pipe, the time required for the sterilization may be reduced.

Figure 2A:
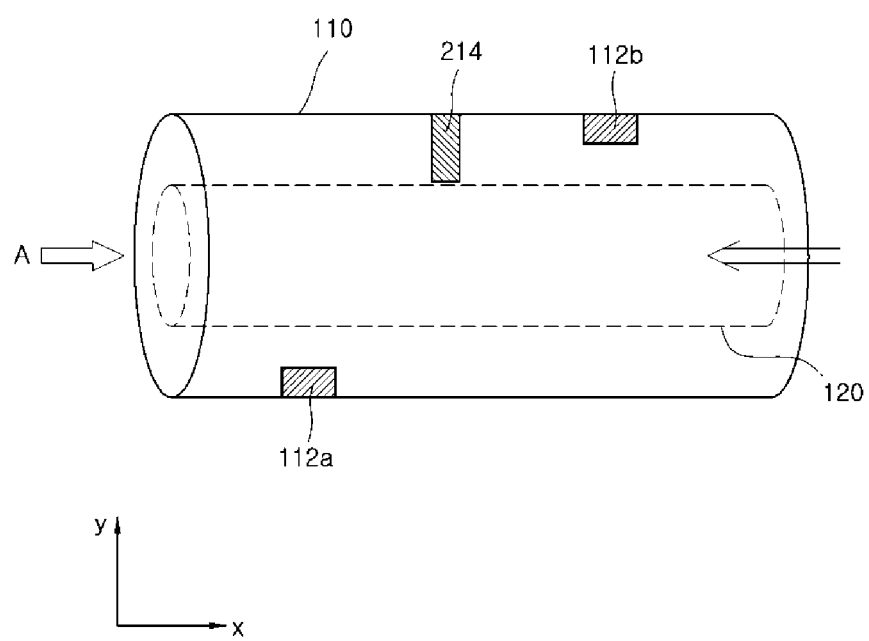
FIG. 2A schematically illustrates an example of a sterilizer in accordance with a second embodiment of the disclosed technology.
Figure 2B:
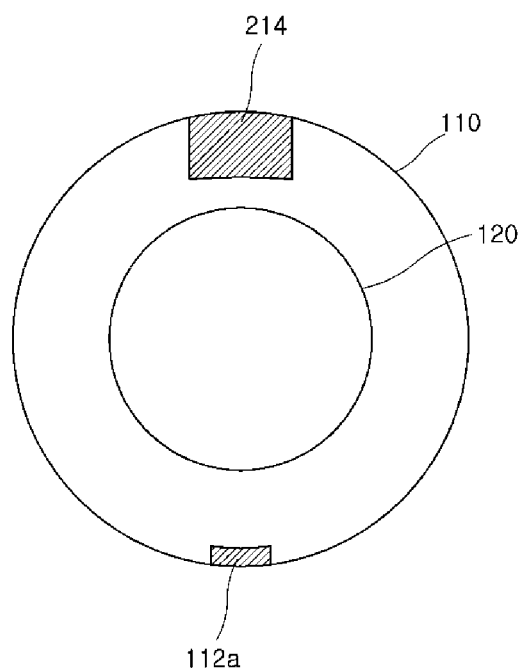
FIG. 2B is a plan view of the sterilizer of FIG. 2A, seen from a direction A.

FIG. 2A schematically illustrates an example of a sterilizer in accordance with a second embodiment of the disclosed technology. FIG. 2B is a plan view of the sterilizer of FIG. 2A that is seen from a direction A.

Referring to FIG. 2A, the sterilizer 200 may include some substantially same structure features as the sterilizer 100 described with reference to FIGS. 1A and 1B and the sterilizer 200 further includes a light reflecting structure 214 disposed on the inner wall of the first pipe 110 between the respective UV light sources 112a, 112b, 112c, and 112d. Thus, the following description will be focused on the structure features in FIGS. 2A and 2B that are different from the sterilizer 100 in FIGS. 1A and 1B in order to avoid duplicate description.

The light reflecting structure 214 may be positioned in the space between the first and second pipes 110 and 120. For example, the light reflecting structure 214 may be positioned in an area inside the first pipe 110 that is not occupied by the second pipe 120. The light reflecting structure 214 reflects the UV light generated from the UV light sources 112a, 112b, 112c, and 112d in cooperation with the UV reflection of the inner wall of the first pipe 110, thereby expanding the area which is covered by the UV light inside the second pipe 120. The light reflecting structure 214 can reduce a non-irradiated area of the UV light, which otherwise may occur in the second pipe 120. FIG. 2A shows one light reflecting structure 214 as an example and multiple light reflecting structures 214 can be implemented. For example, referring back to FIG. 1A, a light reflecting structures 214 can be placed on the top inner wall of the first pipe 110 at a location between LED 112a on the bottom inner wall of the first pipe 110 and LED 112b on the top inner wall of the first pipe 110. This is what is shown in FIGS. 2A and 2B. Additional light reflecting structures 214 can be placed on the top and/or bottom inner wall of the first pipe 110. As a specific example, an additional light reflecting structure 214 can be placed on the bottom inner wall of the first pipe 110 at a location between LED 112a on the bottom inner wall of the first pipe 110 and LED 112b on the top inner wall of the first pipe 110, e.g., at a location opposing the light reflecting structures 214 shown in FIG. 2A. Similar additional light reflecting structures 214 can be placed on the bottom/top inner wall of the first pipe 110 at locations between LED 112b and LED 112c, between LED 112c and LED 112d.

Such light reflecting structures 214 provide light reflecting structures or surfaces beyond the light-reflecting surfaces of the inner walls of the first pipe 110 to reflect the UV light into the interior of the second pipe 120. The light reflecting structures 214 can be structured and arranged to eliminate a non-irradiation area of the UV light within the second pipe that is not illuminated by the UV light, improve the UV illumination uniformity in the second pipe 120 and increase the overall utilization efficiency of the UV light generated by the LEDs.

Referring to FIG. 2B, the light reflecting structure 214 and the UV LEDs 112b and 112d may be arranged in a line on the top inner wall of the first pipe 110 along the X-axis direction, or the light reflecting structure 214 and the UV LEDs 112a and 112c may be arranged in a line on the bottom inner wall of the first pipe 110 along the X-axis direction. However, the disclosed technology is not limited to such a configuration. The arrangement of the light reflecting structure 214 on the inner wall of the first pipe 110 may be modified from what is in FIG. 2B in various manners to provide improved UV illumination in the second pipe 120 for sterilization operation.

The above examples in FIGS. 1A, 1B, 2A and 2B can be used to direct a fluid through a sterilization device by inputting the fluid into the device from one end and outputting the sterilized fluid out of the device from the opposite end. In other designs, the fluid may be directed into and out of the device from the same end as shown by an example in FIG. 3.

Figure 3:
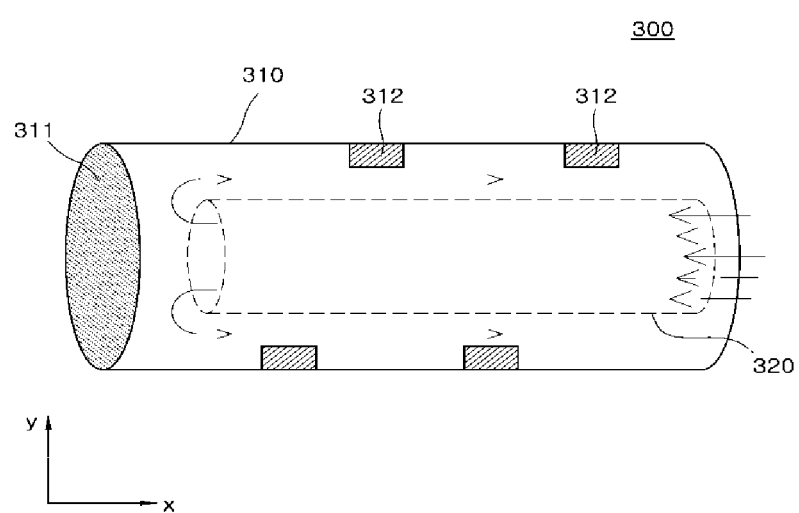
FIG. 3 schematically illustrates an example of a sterilizer in accordance with a third embodiment of the disclosed technology.

FIG. 3 schematically illustrates an example of a sterilizer in accordance with a third embodiment of the disclosed technology. Referring to FIG. 3, the sterilizer 300 includes a first, outer pipe 310 and a second, inner pipe 320 disposed inside the first pipe 310.

In the illustrated example, the first pipe 310 has a closed end 311 at one side of the first pipe 310 and an open end at the other side. Furthermore, the first pipe 310 may include an inner wall having a light reflecting property to reflect the UV light. The closed end 311 may also have a light reflecting property to reflect the UV light. For example, the inner wall and the closed end 311 of the first pipe 310 may be coated with a metal having a high reflectance, such as aluminum or silver.

In the illustrated example, the inner wall of the first pipe 310 includes, or is used to mount or hold, a plurality of UV light sources 312 arranged to provide illumination to the second pipe 120. In some implementations, UV light sources 312 can be configured and arranged in substantially the same manner as the UV LEDs 112a, 112b, 112c, and 112d described in FIGS. 1A and 1B.

The second pipe 320 is disposed inside the first pipe 310, and has a light transmitting property to allow transmission of the UV light through its walls to provide UV illumination of the interior of the second pipe 320. The second pipe 320 may be formed of, or include, for example, quartz or another suitable optically transmissive or optically transparent material to allow the UV light to enter the interior of the second pipe 320. As illustrated by the example in FIG. 3, the fluid to be sterilized is guided into and, flows through, the second pipe 320. The second pipe 320 has two open ends for conducting the fluid with a first opened end that is used to receive the fluid and is positioned separately from the closed end 311 of the first pipe 310 (facing the open end of the first pipe 310). The second open end of the second pipe 320 is to direct the received fluid out of the second pipe 310 and is positioned close to the closed end 311 of the first pipe 310. Due to the above configuration, the flow direction of the fluid flowing through the second pipe 320 is blocked by the closed end 311 of the first pipe 310 and thus is switched in direction or is redirected at the closed end 311 such that the fluid flows along the opposite direction to flow through the space between the first pipe 310 and the second pipe 320. That is, after the fluid reaches at the closed end 311, the fluid turns its direction to be opposite and inversely flows in an area inside the first pipe 310 and outside the second pipe 320. Therefore, the fluid flows through an UV-illuminated section twice in this configuration to receive additional UV exposure that would not be available if the first pipe 310 does not have the closed end 311. This increased UV exposure can improve the sterilization operation.

Although not illustrated in FIG. 3, a driving device may be provided at the opposite end or side of the closed end 311 to generate a driving force that causes the fluid to flow. For example, the driving device may include a fluid treatment pump or a suitable fluid driving mechanism to direct or force the fluid to flow in the direction as illustrated in FIG. 3. The driving device at the opposite end may generate a driving force to pass the fluid through the second pipe 310. Alternatively, the driving device may be provided to generate a driving force that causes the fluid to flow in the space between the first and second pipes 310 and 320 along the X-axis. The driving device may adjust the flow velocity and rate of the fluid.

In the example in FIG. 3, the fluid, which is sterilized by the UV light sources 312 while flowing through the second pipe 320, may be sterilized again by the UV light sources 312 while returning to the opposite end after the flow direction of the fluid is switched at the closed end 311.

Figure 4:
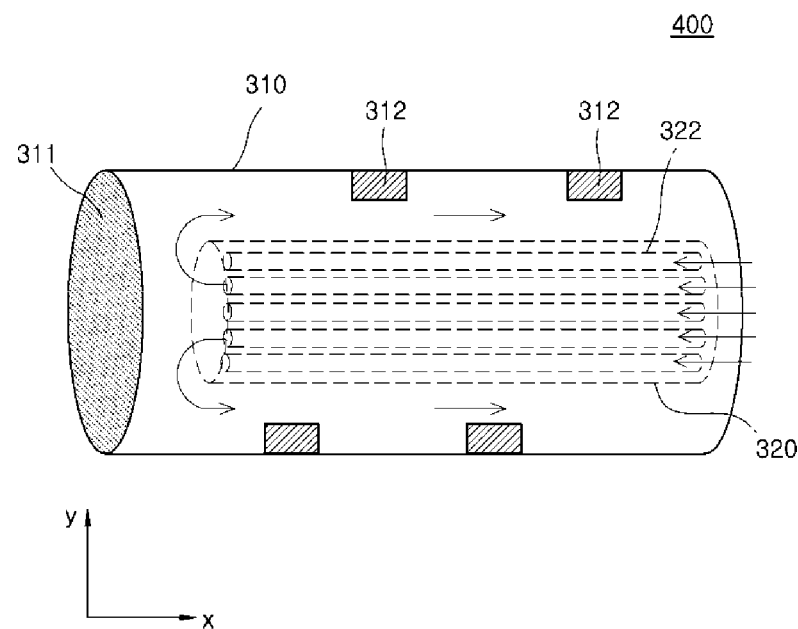
FIG. 4 schematically illustrates an example of a sterilizer in accordance with a fourth embodiment of the disclosed technology.

FIG. 4 schematically illustrates another example of a sterilizer in accordance with a fourth embodiment of the disclosed technology. Referring to FIG. 4, the sterilizer 400 may have substantially the same structure in terms of the construction of the first, outer pipe 310 and the second, inner pipe 320 as the sterilizer 300 of FIG. 3 but inside the second pipe 320 in FIG. 4, two or more inner pipes 322 are placed inside the second pipe 320, which, collectively along with the pipe 320, operate to guide the fluid for UV sterilization.

The sterilizer 400 may sterilize fluid through the UV light sources 312, while the fluid flows through inner pipes 322 and the second pipe 320. Like the second pipe 320, each inner pipe 322 has a light transmitting property to transmit the UV light from the UV light sources 312 to enter the interior of each inner pipe 322 for sterilizing the fluid inside. For example, the inner pipe 322 may be formed of or include quartz or a suitable UV transparent material. In comparison with the device 300 in FIG. 3, each inner pipe 322 in FIG. 4 can be designed to have a smaller pipe size or inner diameter than that of the second pipe 320. Accordingly, with other conditions being equal, as the fluid flows through inner pipes 322, the flow velocity of the fluid inside the second pipe 320 may slow down in comparison with the fluid speed inside the single larger second pipe 320 in FIG. 3, thereby increasing the irradiation time of the UV light per unit volume with respect to the flowing fluid. This increased radiation time can improve the sterilization.

Figure 5:
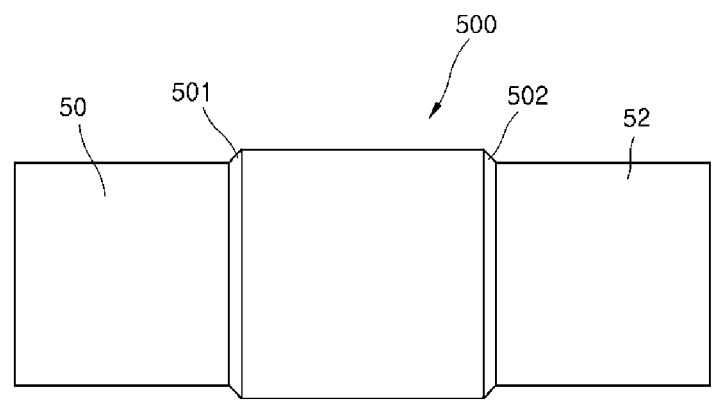
FIG. 5 schematically illustrates an example of a connector in accordance with the fourth embodiment of the disclosed technology.

FIG. 5 schematically illustrates an example of a connector in accordance with the fourth embodiment of the disclosed technology to provide fluid sterilization. Referring to FIG. 5, the connector 500 includes first and second ends or connection ports 501 and 502 coupled to fluid flow pipes 50 and 52, respectively, to connect the fluid flow pipes 50 and 52 to allow for a fluid to flow through the pipes 520 and 52. The interfacing with the pipes 50 and 51 at the first and second ends 501 and 502 may be sealed by using a suitable sealing mechanism, including, e.g., publicly-known sealing members, to prevent fluid leak between the fluid flow pipe 50 of the first end 501 and the fluid flow pipe 52 of the second end 502.

The connector 500 may include substantially the same components as a fluid sterilizer based on the disclosed technology, such as the sterilizer 100 described with reference to FIGS. 1A and 1B or the sterilizer 200 described with reference to FIGS. 2A and 2B. Therefore, the connector 500 can provide fluid sterilization in the fluid that flow between pipes 50 and 51.

The connector 500 may include the sterilizer mounted in the connection parts of the flow fluid pipes 50 and 52, and perform UV sterilization on fluid flowing through the fluid flow pipes 50 and 52.

Figure 6A:
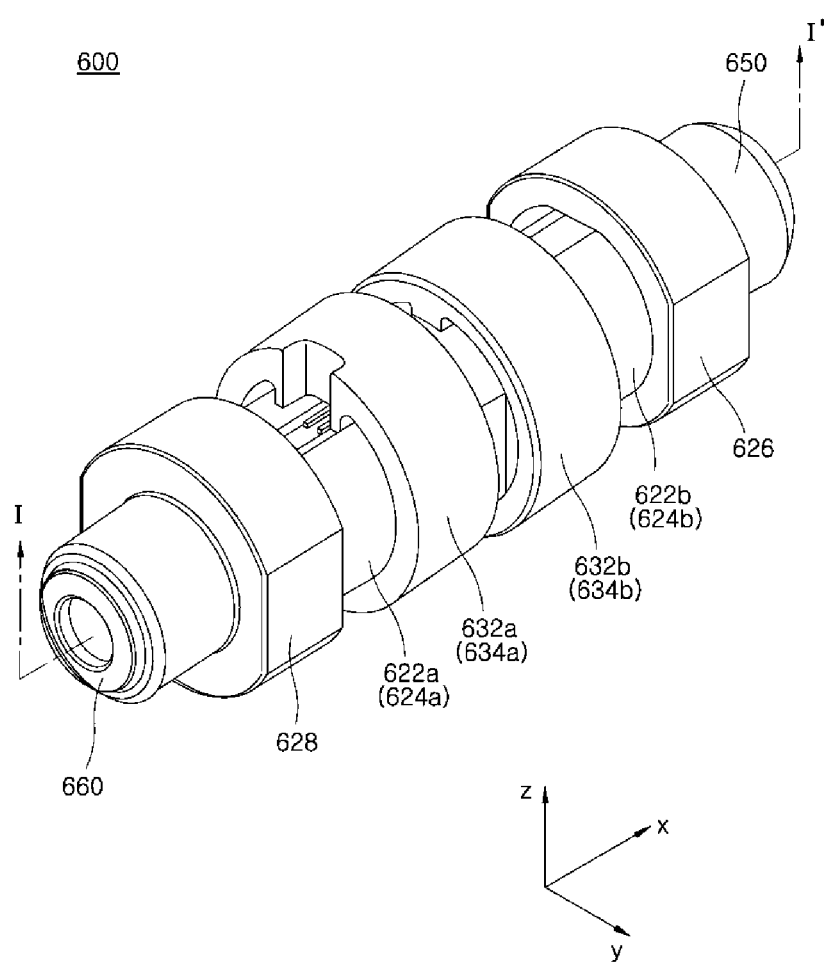
FIG. 6A schematically illustrates an example of a sterilizer in accordance with a fifth embodiment of the disclosed technology.
Figure 6B:
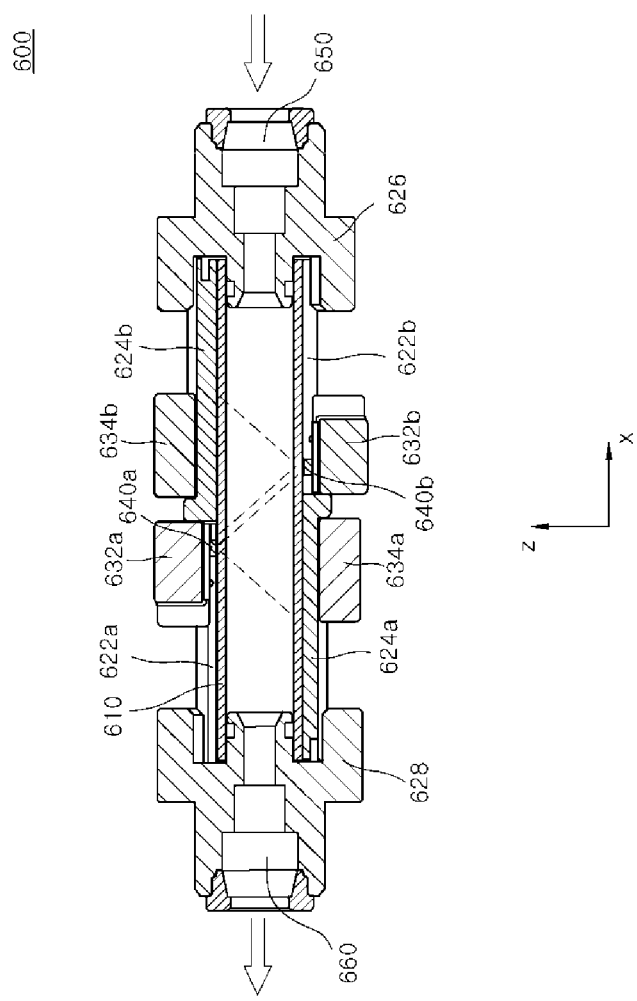
FIG. 6B is a cross-sectional view of the sterilizer of FIG. 6A, taken along line I-I'.

FIG. 6A schematically illustrates an example of a sterilizer in accordance with a fifth embodiment of the disclosed technology. FIG. 6B is a cross-sectional view of the sterilizer of FIG. 6A, taken along line I-I'.

Referring to FIGS. 6A and 6B, the sterilizer 600 includes a light-transmitting fluid flow pipe 610, first body parts 622a, 624a, 622b, and 624b surrounding the light-transmitting fluid flow pipe 610, and UV light sources 640a and 640b for irradiating UV light onto the light-transmitting fluid flow pipe 610 for the sterilization.

The fluid to be sterilized passes through the light-transmitting fluid flow pipe 610 which corresponds to the second pipes 120 and 320 in aforementioned implementations of the present disclosure. Both ends of the light-transmitting fluid flow pipe 610 may be connected to an inlet part 650 for receiving the fluid to be sterilized and an outlet part 660 for exporting the UV-treated and sterilized fluid, respectively.

The first body parts 622a, 624a, 622b, and 624b may be arranged to surround the outside of the light-transmitting fluid flow pipe 610. The first body parts 622a, 624a, 622b, and 624b may be coupled to a second body part 626 for fixing the inlet part 650 and a third body part 628 for fixing the outlet part 660. In another implementation, the first body parts 622a, 624a, 622b, and 624b may be integrated with the second body part 626 and the third body part 628.

The first body parts 622a, 624a, 622b, and 624b may be arranged along the longitudinal direction of the light-transmitting fluid flow pipe 610, and may be divided into two or more units. Specifically, for example, FIG. 6A illustrates a first unit 622a and 624a and a second unit 622b and 624b as separate units. As described below, movable units 632a, 634a, 632b, and 634b coupled to UV light sources 640a and 640b are provided and are disposed at a part 622a and 622b of the first and second units 622a, 624a, 622b, and 624b. Such movable units enable adjustment of positions of the UV light sources in the sterilization operation.

The movable units 632a, 634a, 632b, and 634b may be coupled to the first body part 622a, 624a, 622b, and 624b. As illustrated in FIGS. 6A and 6B, the movable units 632a, 634a, 632b, and 634b may include a ring-shaped structure. The UV light sources 640a and 640b may be mounted on at least some of the movable units 632a, 634a, 632b, and 634b. For example, in FIG. 6B, the UV light sources 640a and 640b are provided on the movable units 632a and 632b. The movable units 632a, 634a, 632b, and 634b may be moved along the longitudinal direction of the first body parts 622a, 624a, 622b, and 624b. Thus, the positions of the UV light sources 640a and 640b coupled to the movable units 632a, 634a, 632b, and 634b may be changed. In the illustrated implementation, the movable units 632a, 634a, 632b, and 634b may include a first movable unit 632a and 634a and a second movable unit 632b and 634b. The first movable unit 632a and 634a and the second movable unit 632b and 634b may be separately moved on the first body parts 622a, 624a, 622b, and 624b. As such, the movable units 632a, 634a, 632b, and 634b may adjust the spatial interval between the UV light sources 640a and 640b on the first body parts 622a, 624a, 622b, and 624b.

The UV light sources 640a and 640b may emit UV light with a wavelength of about 200 nm to 400 nm. For example, the UV light sources 640a and 640b may emit UV light with a wavelength of about 200 to 290 nm. In one implementation, the UV light sources 640a and 640b may include UV LEDs. The UV light sources 640a and 640b may be arranged in substantially the same manner as the arrangement of the UV light sources 112a, 112b, 112c, and 112d in the sterilizer 100 of FIG. 1A. The UV light emitted from the UV light sources 640a and 640b may sterilize fluid flowing through the light-transmitting fluid flow pipe 610.

The inlet part 650 may be disposed in the second body part 626 to transfer fluid from outside into the light-transmitting fluid flow pipe 610. The inlet part 650 may include a pipe-shaped structure. The fluid flowing through the light-transmitting fluid flow pipe 610 may be sterilized by UV light emitted from the UV light sources 112a, 112b, 112c, and 112d. The sterilized fluid may be discharged to the outside through the outlet part 660. The outlet part 660 may be disposed in the third body part 628, and include a pipe-shaped structure.

FIGS. 7A to 7C illustrate the arrangement of the UV light sources of the sterilizer in accordance with one implementation of the present disclosure. As illustrated in FIGS. 7A to 7C, the positions of the UV light sources 640a and 640b may be changed according to the movement of the first movable unit 632a and 634a and the second movable unit 632b and 634b. Referring to FIG. 7A, the UV light sources 640a and 640b may be remote from each other to have a first distance r1 along a X-axis. As the first movable unit 632a and 634a and the second movable unit 632b and 634b are moved in the opposite directions away from each other along the X-axis, the distance between the UV light sources 640a and 640b may be changed to a second distance r2 of FIG. 7B or a third distance r3 of FIG. 7C.

In the case of FIG. 7A, since the distance between the UV light sources 640a and 640b is relatively small, UV lights emitted from the UV light sources 640a and 640b may overlap each other. Thus, the density of the UV light irradiated onto the fluid may be higher than those in FIGS. 7B and 7C. In the case of FIG. 7C, the sterilization efficiency around the inlet part 650 and the outlet part may become higher as compared to FIGS. 7A and 7B.

Figure 8A:
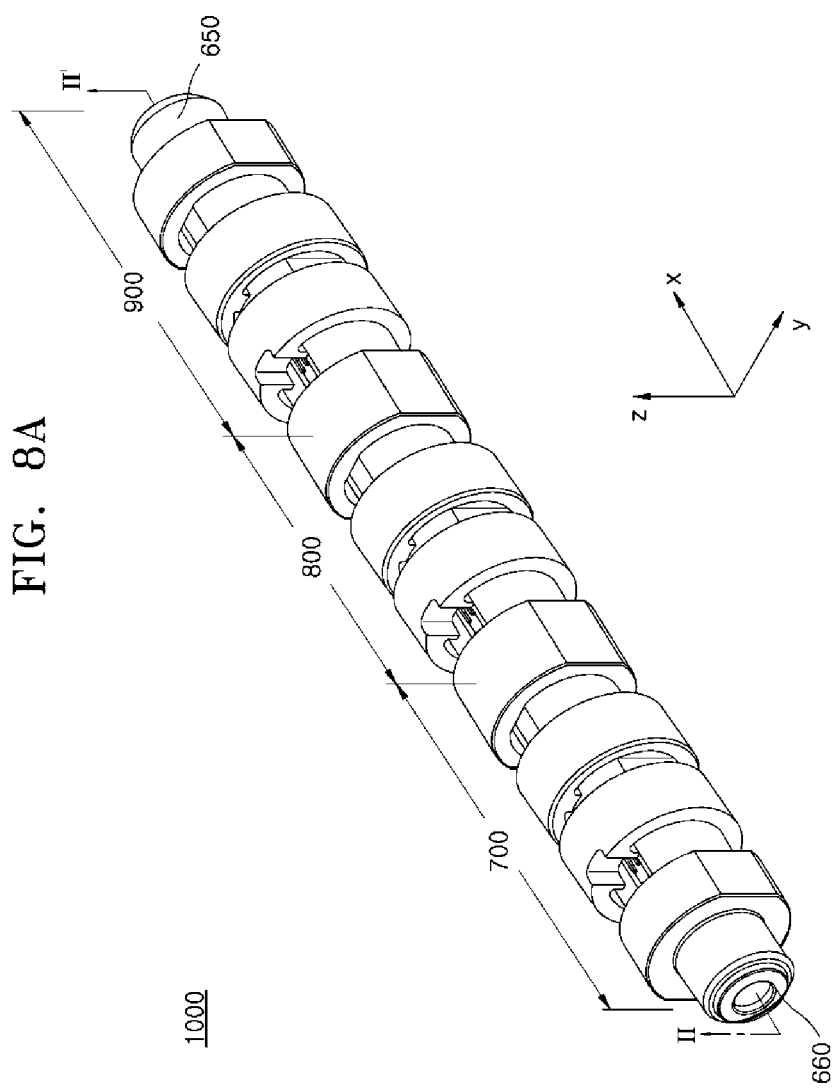
FIG. 8A is a schematic perspective view of an example of a sterilizer in accordance with a sixth embodiment of the disclosed technology.
Figure 8B:
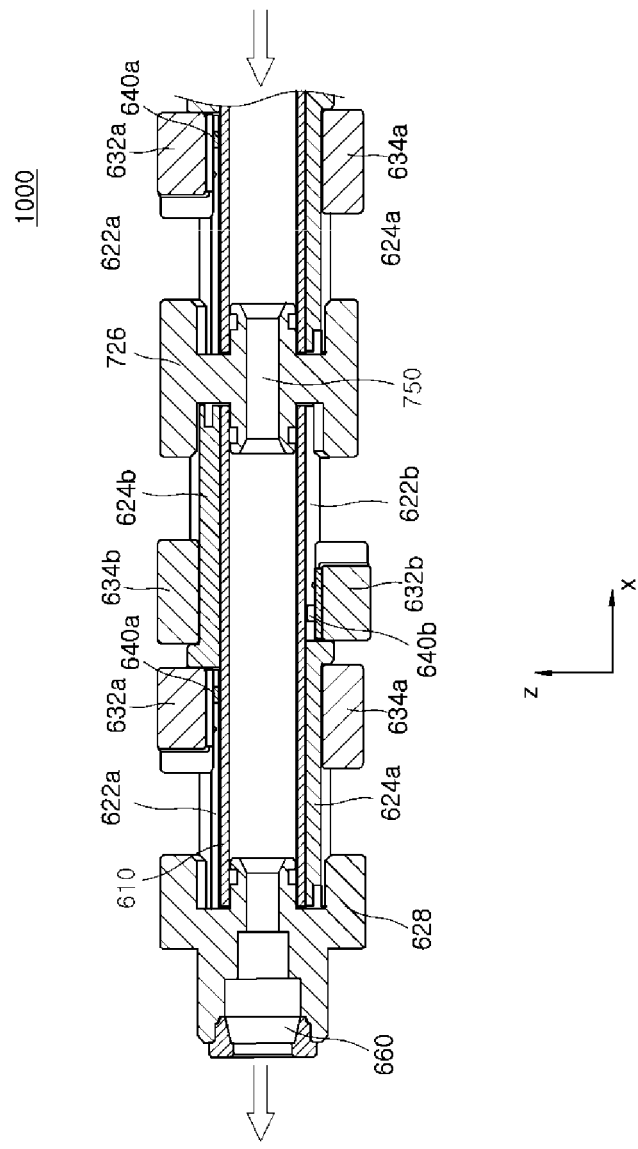
FIG. 8B is a cross-sectional view of the sterilizer of FIG. 8A, taken along line II-II'.

FIG. 8A is a schematic perspective view of a sterilizer in accordance with one implementation of the present disclosure. FIG. 8B is a cross-sectional view of the sterilizer of FIG. 8A, which is taken along line II-II'.

The sterilizer 1000 illustrated in FIGS. 8A and 8B includes sterilization modules that are coupled in series. The sterilizer 1000 may include a first sterilization module 700, a second sterilization module 800, and a third sterilization module 900. Each of the sterilization modules 700, 800, and 900 may correspond to the sterilizer 600 shown in FIGS. 6A and 6B. To connect sterilization modules to each other, a connection pipe may be provided between two serially arranged connection modules. For example, between the first and second sterilization modules 700 and 800 and between the second and third sterilization modules 800 and 900, connection pipes 750 may be disposed to connect second pipes 610 of the sterilization modules 700, 800, and 900, respectively.

The sterilizer 1000 may include an inlet part 650 for introducing fluid and an outlet part 660 for discharging sterilized fluid. FIG. 8B illustrates the detailed structure of the connection part between the first and second sterilization modules 700 and 800. At the connection part between the first and second sterilization modules 700 and 800, a second body part 726 may be disposed to fix the light-transmitting fluid flow pipe 610. An inlet part or outlet part may not be separately provided at the connection part between the first and second sterilization modules 700 and 800, but other implementations are also possible.

FIG. 8A illustrates that the sterilizer 1000 includes three sterilization modules 700, 800, and 900, but other implementations are also possible on the number of sterilization modules included in the sterilizer 1000. each sterilization module may be formed as described with regard to the sterilizer 700 in FIG. 7 and then a plurality of sterilization modules 700 may be connected in series.

Although examples of various embodiments and implementations, including preferred embodiments, of the disclosed technology have been disclosed for illustrative purposes, those skilled in the art will appreciate that various modifications, additions and substitutions are possible.

What is claimed is:
1. A sterilizer for sterilizing a liquid, comprising:
a first pipe having a closed end and an opposite, open end;
a second pipe disposed in the first pipe and having a light transmitting property to transmit ultraviolet (UV) light; and
a plurality of UV LEDs engaged to and arranged in the first pipe and configured to provide UV light to a fluid flowing through the inside of the second pipe or the space between the first and second pipes to cause sterilization of the fluid, wherein the plurality of UV LEDs are arranged in a zigzag pattern on the inner wall of the first pipe in consideration of beam angles of UV beams emitted by the UV LEDs in order to provide desired UV illumination coverage within the second pipe, wherein the second pipe includes two or more inner pipes placed inside the second pipe.

2. The sterilizer of claim 1, wherein the inner wall of the first pipe reflects the UV light.

3. The sterilizer of claim 1, further comprising a plurality of inner pipes inside the second pipe to pass the fluid and each inner pipe transmits the UV light.

4. The sterilizer of claim 1, wherein the second pipe has an opened end disposed separately from the closed end of the first pipe.

5. The sterilizer of claim 1, wherein each of the UV LEDs is positioned within a beam of another UV LED disposed on the inner wall at the opposite side, the beam angle ranging from 110° to 140°.

6. The sterilizer of claim 1, wherein the first pipe includes aluminum, and the second pipe includes quartz.

7. A connector having a function of sterilizing a liquid, comprising:
a first pipe having an inner wall that reflects ultraviolet (UV) light;
a plurality of UV light emitting diodes (LEDs) arranged on the inner wall that produce UV light;
a second pipe disposed in the first pipe to pass a fluid therethrough, and structured to transmit the UV light from the UV LEDs into an interior of the second pipe to cause sterilization of the fluid;

connection parts on both ends of the connector to connect two external fluid flow pipes to guide the fluid between the two external fluid flow pipes, wherein the UV LEDs are arranged to position on opposite sides of the inner wall of the first pipe in a way that each UV LED is placed within a beam of another UV LED located on an opposite side; wherein the second pipe includes two or more inner pipes placed inside the second pipe.

8. The connector of claim 7, wherein the UV LEDs are arranged in a zigzag pattern on the inner wall of the first pipe.

9. A sterilizer for sterilizing a fluid, comprising:
a light-transmitting fluid flow pipe having a side wall that transmits ultraviolet (UV) light to a fluid inside the light-transmitting fluid flow pipe to be sterilized;
movable units mounted outside of the light-transmitting fluid flow pipe; and
UV light sources mounted on the movable units to provide UV light for sterilizing the fluid flowing through the light-transmitting fluid flow pipe,
wherein the movable units adjust the distance between the UV light sources,
wherein the movable units mounted outside of the light-transmitting fluid flow pipe are coupled to the light-transmitting fluid flow pipe to move along a longitudinal direction of the light-transmitting fluid flow pipe.

10. The sterilizer of claim 9, comprising:
a body part mounted to the outside of the light-transmitting fluid flow pipe, and
wherein each movable unit includes a ring-shaped structure surrounding the body part, and is movable along a longitudinal direction of the body part.

* * * * *